US006654117B1

(12) United States Patent
Reading

(10) Patent No.: US 6,654,117 B1
(45) Date of Patent: Nov. 25, 2003

(54) BOTTLE CAP SENSOR APPARATUS AND METHOD

(75) Inventor: Michael J. Reading, Atlanta, GA (US)

(73) Assignee: The Quaker Oats Company, Chicago, IL (US)

( * ) Notice: Subject to any disclaimer, the term of this patent is extended or adjusted under 35 U.S.C. 154(b) by 95 days.

(21) Appl. No.: 09/946,373

(22) Filed: Sep. 4, 2001

(51) Int. Cl.$^7$ .............................................. G01N 21/00
(52) U.S. Cl. ................... 356/240.1; 250/223 B
(58) Field of Search .................. 356/240.1, 239.4, 356/239.7, 239.8, 428; 250/223 B

(56) References Cited

U.S. PATENT DOCUMENTS

| | | |
|---|---|---|
| 2,689,646 A | 9/1954 | Dilliard |
| 3,469,689 A | 9/1969 | O'Neill, Jr. |
| 4,355,724 A | 10/1982 | Erdman et al. ............. 209/529 |
| 4,511,044 A | 4/1985 | Connor et al. ............. 209/522 |
| 4,521,807 A | 6/1985 | Werson ....................... 358/106 |
| 4,691,496 A | 9/1987 | Anderson et al. ............... 53/53 |
| 4,746,212 A | 5/1988 | Sudo et al. .................. 356/240 |
| 4,772,128 A | 9/1988 | Vinarub et al. ............. 356/384 |
| 4,773,204 A | 9/1988 | Rydstrom ..................... 53/506 |
| 4,872,300 A | 10/1989 | Luke ............................. 53/53 |
| 5,010,760 A | 4/1991 | Nish et al. .................... 73/1 H |
| 5,214,953 A | 6/1993 | Nish et al. .................... 73/1 H |
| 5,489,987 A | 2/1996 | Ringlien ..................... 356/428 |
| 5,591,462 A | 1/1997 | Darling et al. .............. 425/173 |
| 5,714,998 A | 2/1998 | Wheeler ....................... 348/92 |
| 5,749,201 A | 5/1998 | Cochrane ..................... 53/281 |
| 6,473,170 B2 * | 10/2002 | Schafer .................... 356/240.1 |

* cited by examiner

Primary Examiner—Russell Adams
Assistant Examiner—Andrew Sever
(74) Attorney, Agent, or Firm—Ryndak & Suri

(57) ABSTRACT

An apparatus for detecting miscapped bottles for use in a bottle line comprises a bottle cap position detector system having signal emitters and signal detectors. The signal emitters are positioned adjacent a conveyor transporting bottles so as to direct signals to different cap target locators. The presence or the absence of a signal detected by the signal detectors indicates one or more incorrect cap positions.

13 Claims, 8 Drawing Sheets

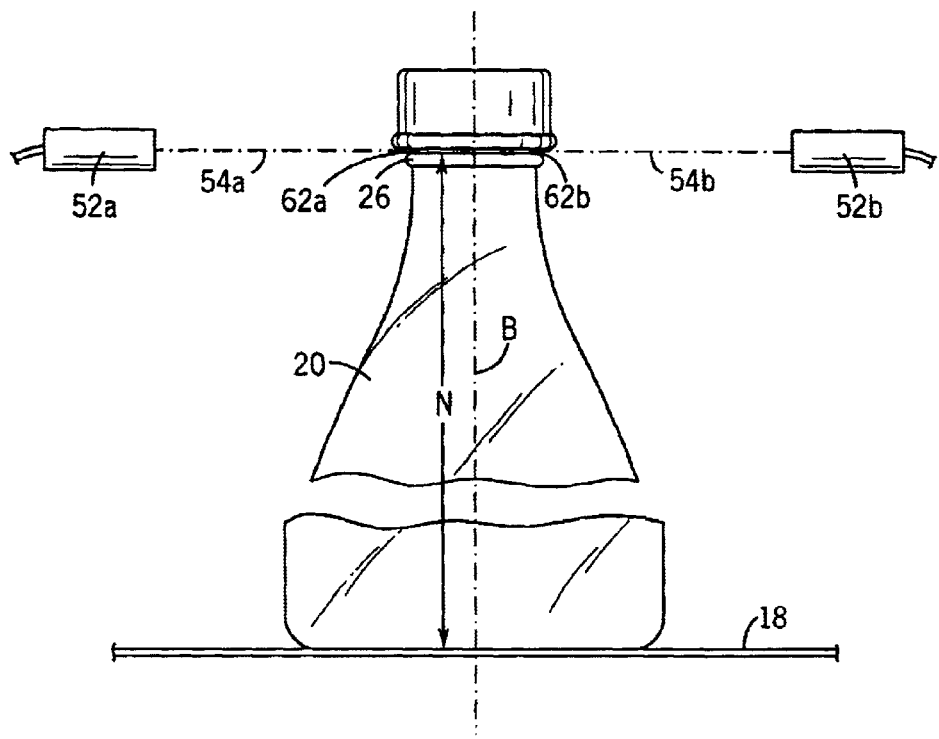
FIG. 5a
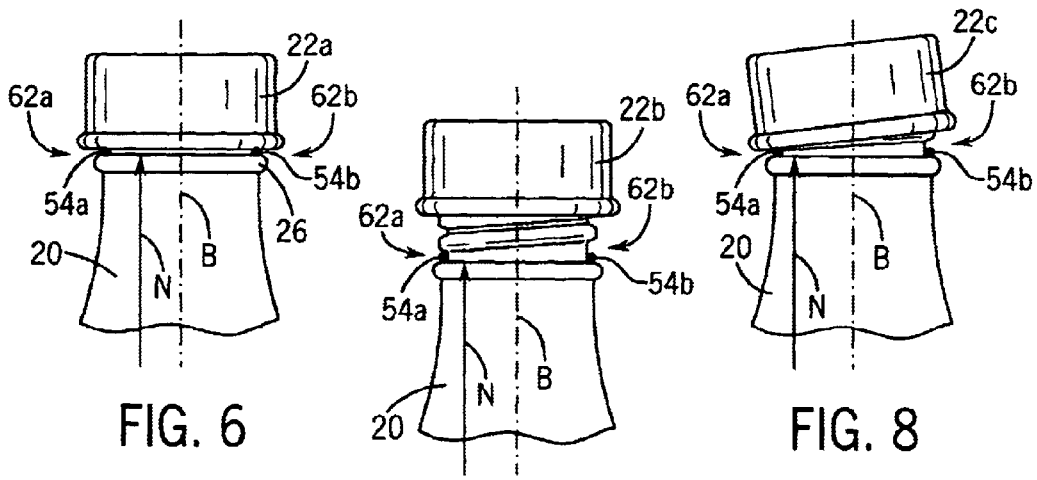
FIG. 6
FIG. 7
FIG. 8

BOTTLE CAP SENSOR APPARATUS AND METHOD

FIELD OF THE INVENTION

The invention relates to an apparatus and method for detecting improperly capped bottles, and in particular to a signal emission and detection device that detects substantially all low cap, high cap, or cocked cap bottles regardless of the bottle cap radial orientation relative to the detection device.

BACKGROUND OF THE INVENTION

In the automated process of filling and capping bottles, it is of substantial importance to detect a miscapped bottle so that such a product can be removed from production. An improperly sealed bottle may not properly protect the bottle contents from microbial activity. An unsealed bottled product is generally not acceptable. Moreover, air sensitive bottled liquids, whether pasteurized or hot fill, may spoil without proper capping.

An undetected miscapped bottle may also result in fluid leakage from the bottle particularly during high-speed bottling production processes. Miscapped bottles may readily spill their contents onto production equipment resulting in heightened production costs due to additional clean-up efforts. Leakage from miscapped containers may damage production equipment thereby requiring unscheduled production downtime to isolate the damage and repair the equipment.

One current method utilized to detect miscapped bottles is photodetection. Photodetection typically entails placing a single photoemitter and photoreceiver on opposing sides of a conveyor transporting capped bottles. The photoemitter has a light source and directs a beam of light to the photoreceiver. The photoemitter and photoreceiver are interconnected to a controller such that various parameters of the bottle can then be monitored by the interruption or noninterruption of the light beam. For instance, a photodetector can be placed at a position such that the light beam impacts the cap when a bottle has a cap. A bottle passing through the detector without a cap would not interrupt the light beam. In this scenario, the controller would generate a "no cap" signal. In a similar manner, photodetection systems are employed to detect a high cap, a low cap or a cocked cap.

Despite these varied applications, a high percentage of miscapped bottles escape detection by current photodetection systems. Oftentimes, the photodetector is unable to distinguish between a properly sealed cap and an improperly sealed cap. For instance, current photodetection systems cannot distinguish between a properly sealed cap and a bottle with a cocked cap when the cap gap is in line with the photodetector's light beam. Both types of bottles can pass through the photodetection system as properly capped.

A need therefore exists for an apparatus and method that can detect substantially all miscapped bottles in a bottle line process. Subsequently, a need exists for an apparatus and method that can distinguish between properly capped bottles and miscapped bottles. More specifically, a need exists for an apparatus and method that can detect a miscapped bottle regardless of the cap's radial orientation relative to the system designed to detect it.

BRIEF SUMMARY OF THE INVENTION

The present invention provides an apparatus and method that detects an improperly capped bottle regardless of the cap's radial orientation relative to the detecting apparatus. The apparatus comprises at least two signal emitters wherein each emits a signal beam to a signal detector. Each emitter is positioned to direct the signal beam to a different cap target location. Each emitter is further positioned at a predetermined height. This height is based upon the height of a properly positioned cap relative to the bottle. Generally, the apparatus positions the emitters so that the signal beams are in a plane normal or substantially normal to the vertical axis of the bottle. The signal beams are radially spaced from each other so that the detector is able to identify a proper cap, high cap, low cap, or a cocked cap by either the presence or absence of detection of the signal beam.

In accordance with another aspect of the invention, the emitters operate simultaneously when directing their respective signal beams to the detectors.

In accordance with another aspect of the invention the signal beam is a highly focused narrow beam of light. Any light source may be utilized by the present invention including, but not limited to, laser, x-ray, visible, ultraviolet, infrared or far red, for example.

In accordance with another embodiment of the present invention, the signal beams are directed across the plane defined by the top of a properly placed cap.

In accordance with another aspect of the invention, the angle of radial spacing between emitters is in the range of about 45 degrees and about 90 degrees.

In accordance with another embodiment of the present invention, the signal beams are directed at target points that are tangential to the plane defined by the bottom of a properly placed cap.

In accordance with another embodiment of the present invention, the bottle cap has a circumferential reflective or absorptive band located on the side of the bottle cap. The signals are emitted at target points that are located on this reflective band for a properly placed bottle cap. A properly positioned cap is detected by the presence or absence of a signal beam reflected off of the reflective or absorptive band.

In accordance with another aspect of the present invention, a method of detecting an improperly capped bottle is provided comprising the steps of:

Providing a detector system having two signal emitters and two corresponding signal detectors; positioning each signal emitter to direct a signal to a different cap target location; directing the signals at a predetermined height relative to the cap in a plane normal to the vertical cap axis; and indicating whether the presence or absence of a signal detected by the signal detector is one or more incorrect cap positions selected from the group consisting of high cap, low cap and cocked cap.

BRIEF DESCRIPTION OF THE DRAWINGS

FIG. 5a is a side view of a properly capped bottle in accordance with an alternate embodiment of the present invention.

FIG. 6 is a side view of the detection of a properly capped bottle in accordance with an alternate embodiment of the present invention.

FIG. 7 is a side view of the detection of a high cap in accordance with an alternate embodiment of the present invention.

FIG. 8 is a side view of the detection of a cocked cap in accordance with an alternate embodiment of the present invention.

DETAILED DESCRIPTION OF THE INVENTION

Figure 1:
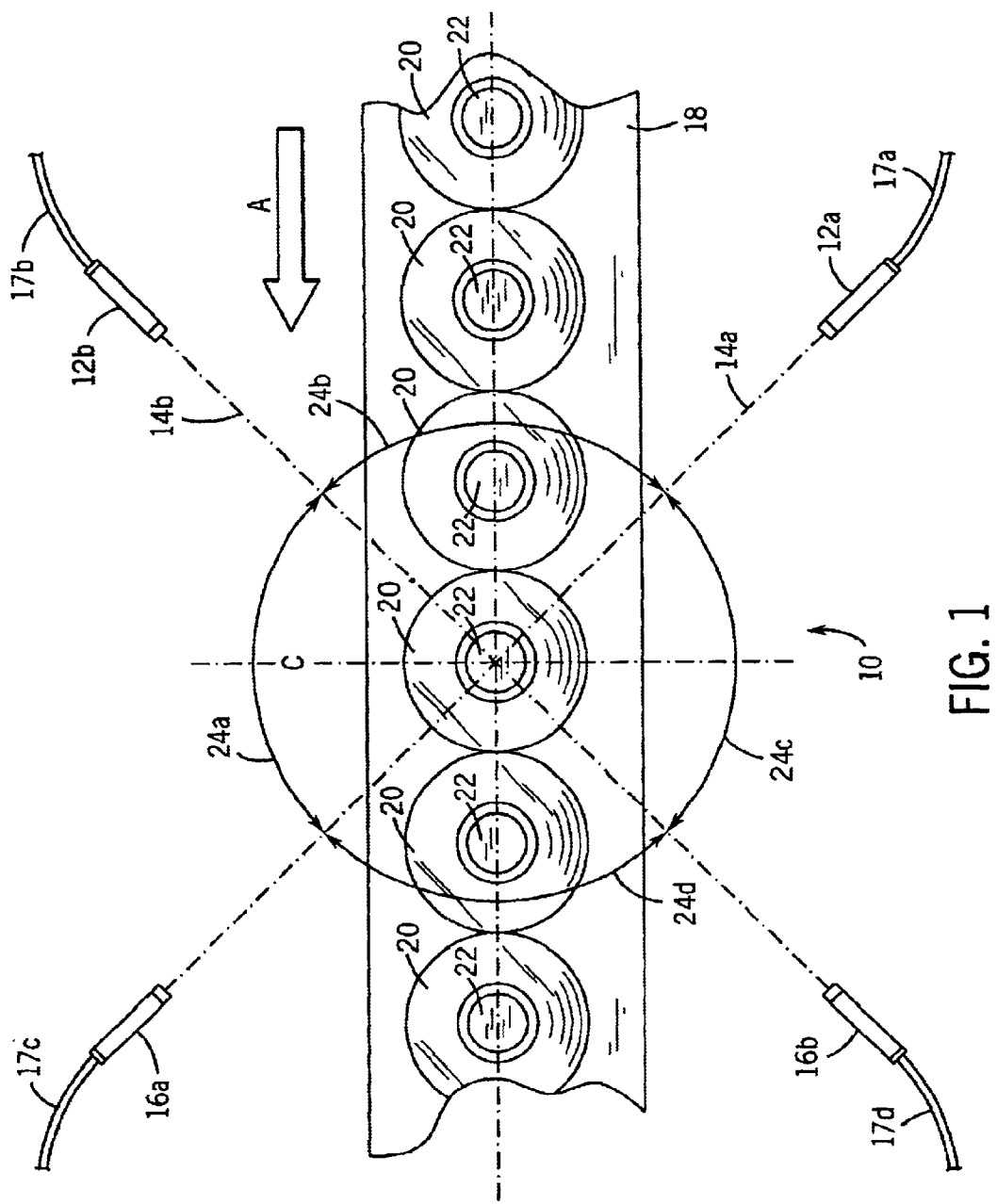
FIG. 1 is a plan view of the miscapped bottle cap detection device in accordance with the present invention.

Referring to the Figures generally, where like reference numerals denote like structure and elements, and in particular to FIG. 1 wherein a miscapped bottle detecting device 10 is illustrated. Device 10 comprises two signal emitters 12a and 12b which emit signal beams 14a and 14b to two signal detectors 16a and 16b. The emitters and detectors operate in pairs such that signal detector 16a is positioned to detect the presence or absence of signal beam 14a from emitter 12a. Likewise, detector 16b is positioned to detect the presence or absence of signal 14b emitted by emitter 12b. Device 10 may alternatively comprise more than two emitter-detector pairs. Each emitter may be aligned linearly with respect to its mated detector as shown in FIG. 1. Alternatively, the emitter-receiver pair may be arranged in a non-linear manner. This will be more fully described in an alternate embodiment of the present invention.

Wires 17a, 17b, 17c and 17d operatively connect emitter 12a, emitter 12b, detector 16a and detector 16b, respectively, to a controller (not shown). The controller coordinates the timing and control of signal emission and detection. For example, the controller activates detectors 16a and 16b to detect signal beams 14a and 14b, respectively, only when the emitters 12a and 12b emit signal beams 14a and 14b, respectively. The controller is programmable and may be programmed to generate a signal when detector 16a receives signal beam 14a from emitter 12a. Alternatively, the controller can be programmed to generate a signal when detector 16a does not receive signal beam 14a from emitter 12a. The controller may be programmed to define signal detection for emitter 12b and detector 16b in a similar manner.

The signal emitted by emitters 12a and 12b may be any suitable signal capable of distinguishing between the narrow tolerances of a properly capped versus a miscapped bottle as is commonly known to those skilled in the art. Typically, the tolerance between a miscapped bottle and a properly capped bottle is on the order of tenths or hundredths of a millimeter. It has been found that the emission and corresponding detection of highly focused, narrow beams of light is capable of distinguishing between a proper cap and a miscapped bottle within these narrow parameters. As such, light sources including, but not limited to, laser, x-ray, ultra-violet, visible, infrared or far red may be employed as the signal beam in accordance with the present invention. Favorable results have been achieved when utilizing the FT-100 Inspection Head manufactured by Industrial Dynamics International Corporation in accordance with the present invention.

Figure 1A:
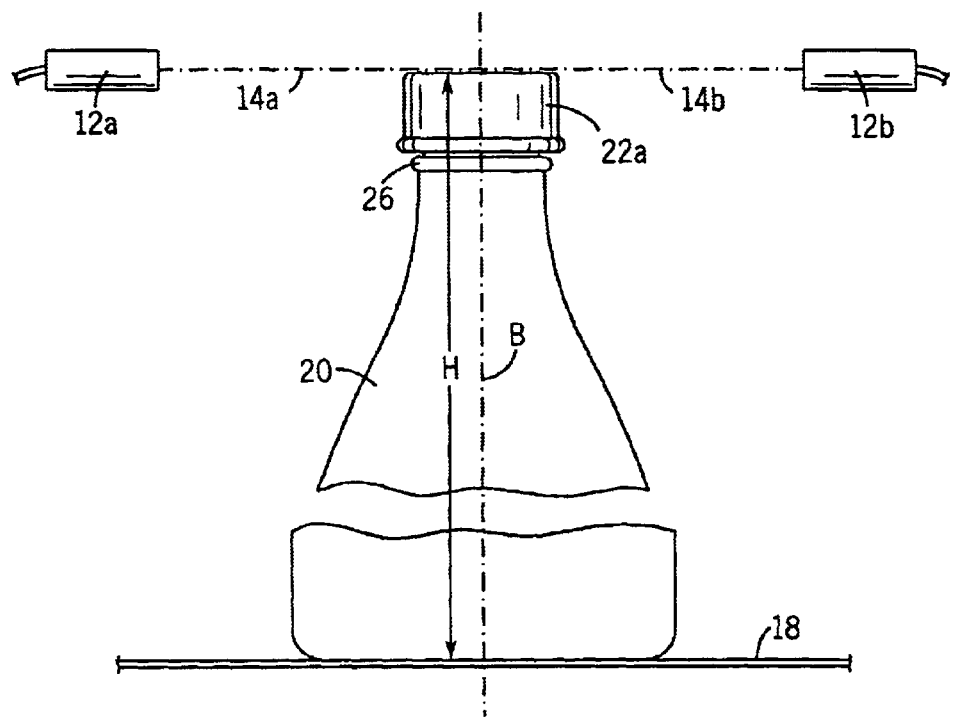
FIG. 1a is a side view of a properly capped bottle in accordance with the present invention.

Conveyor 18 transports bottle 20 having bottle cap 22 thereon in the direction of motion indicated by arrow A. Correctly positioned cap 22a on bottle 20 defines a vertical cap axis B as shown in FIG. 1a. Correctly positioned cap 22a on bottle 20 also defines the correct cap height H relative to bottle 20. As shown in FIGS. 1 and 1a, emitters 12a and 12b are located above and adjacent to conveyor 18 and are suitably mounted so that signal beams 14a and 14b, respectively, are normal to vertical axis B. In addition, emitters 12a and 12b are positioned to emit signal beams 14a and 14b at a proximate height H relative to bottle 20. Preferably, bottle 20 is delivered to device 10 by conveyor 18 so that vertical axis B of bottle 20 is normal to signal beams 14a and 14b when emitted by emitters 12a and 12b.

Emitters 12a and 12b may be positioned in any suitable configuration such that signal beams 14a and 14b are directed to different target locations of cap 20. For example, emitters 12a and 12b may be located on the same side of conveyor 18. In this configuration, a single signal detector may be utilized. Preferably, emitters 12a and 12b are coplanar and located on opposite sides of conveyor 18 thereby straddling conveyor 18. FIG. 1 illustrates this configuration wherein emitter 12a is on the same side of conveyor 18 as detector 16b. Likewise, emitter 12b is on the same side of conveyor 18 as detector 16a. This arrangement results in the intersection of beams 14a and 14b and produces intersect angles 24a, 24b, 24c and 24d.

Intersect angles 24a, 24b, 24c, 24d may range between about 45 degrees to about 135 degrees. It has been found that positioning emitters 12a and 12b so that angles 24a, 24b, 24c and 24d are each 90 degrees provides device 10 with the ability to detect substantially all high capped or cocked capped bottles regardless of the radial orientation of the bottle or the cap relative to the detection apparatus (typically reference to one of the bottle or cap includes the other, since typically once capped, even if incorrectly capped, the cap does not move relative to the bottle).

Conveyor 18 transports bottle 20 having cap 22 to detection point C as shown in FIG. 1. A sensor (not shown) operatively connected to the controller sends a signal to the controller that bottle 20 is located at detection point C. The controller then instructs emitters 12a and 12b to emit signal beams 14a and 14b, respectively. Detection of signal beams 14a and 14b by signal detectors 16a and 16b, respectively, depends upon the placement of cap 22 upon bottle 20.

Figure 2:
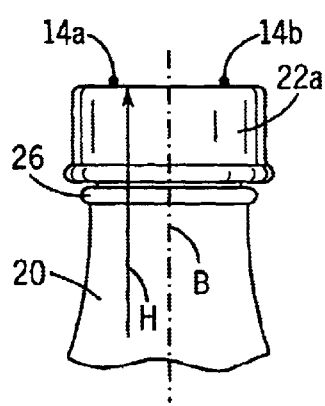
FIG. 2 is a side view of the detection of a properly capped bottle in accordance with the present invention.

FIG. 2 shows the beam detection profile for cap 22a when properly placed upon bottle 20. Emitters 12a and 12b direct signal beams 14a and 14b to traverse the plane defined by the top of properly placed cap 22a on bottle 20 without impingement. Signal detectors 16a and 16b thereby detect signal beams 14a and 14b, respectively. The controller is programmed to interpret this detection profile as a properly capped bottle.

Figure 3:
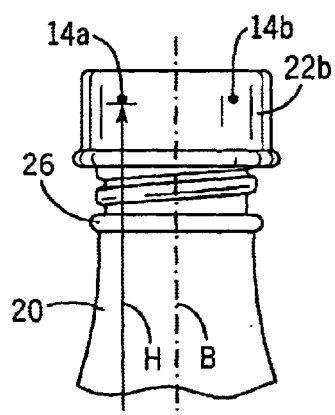
FIG. 3 is a side view of the detection of a high cap in accordance with the present invention.

FIG. 3 illustrates the beam detection profile for high cap 22b. Since emitters 12a and 12b are positioned to deliver signal beams 14a and 14b, respectively, at height H, signal beams 14a and 14b are both prevented from traversing the plane defined by the top of a properly placed cap since cap 22b extends beyond height H. Signal detectors 16a and 16b therefore do not detect signal beams 14a and 14b. The controller is correspondingly programmed to interpret this detection profile as a high capped or miscapped bottle. As such, the controller may generate a signal indicating a miscapped bottle as desired.

Figure 4:
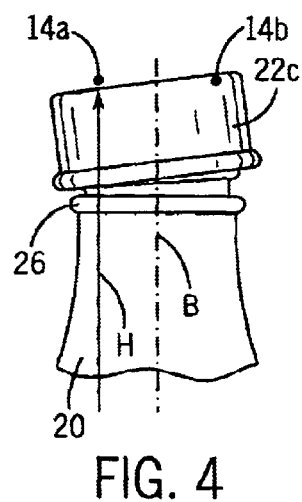
FIG. 4 is a side view of the detection of a cocked cap in accordance with the present invention.

FIG. 4 depicts the beam detection profile for cocked cap 22c. Signal beam 14a traverses the plane defined by the plane of the top of a properly placed cap at height H. Signal beam 14a is thereby detected by signal detector 16a. Signal beam 14b, however, is interrupted as a portion of cap 22c extends beyond height H. Signal detector 16b therefore does not detect signal beam 14b. The controller is programmed to interpret this detection profile as a miscapped bottle.

The controller may be programmed to indicate these various detection beam profiles by any method commonly known to those skilled in the art. For example, the controller may be operatively connected to a plurality of different colored lights to indicate a proper cap (i.e., green) a high cap (i.e., red) or a cocked cap (i.e., red). Or, the controller may be operatively connected to a display screen that indicates the occurrence of a proper cap, a high cap or a cocked cap. The display screen may be positioned so that a person monitoring the bottling and capping production process may also monitor the occurrence of miscapped bottles.

Preferably, the controller is operatively connected to a discharge gate downstream of device 10 on conveyor 18. Upon detection of high cap 22b or cocked cap 22c by device 10, the controller sends a signal to a discharge gate (not shown). When the miscapped bottle arrives at the discharge gate on conveyor 18, the discharge gate directs the miscapped bottle to a discharge conveyor. The miscapped bottle is thereby automatically segregated or discharged from the bottling production line.

Figure 5:
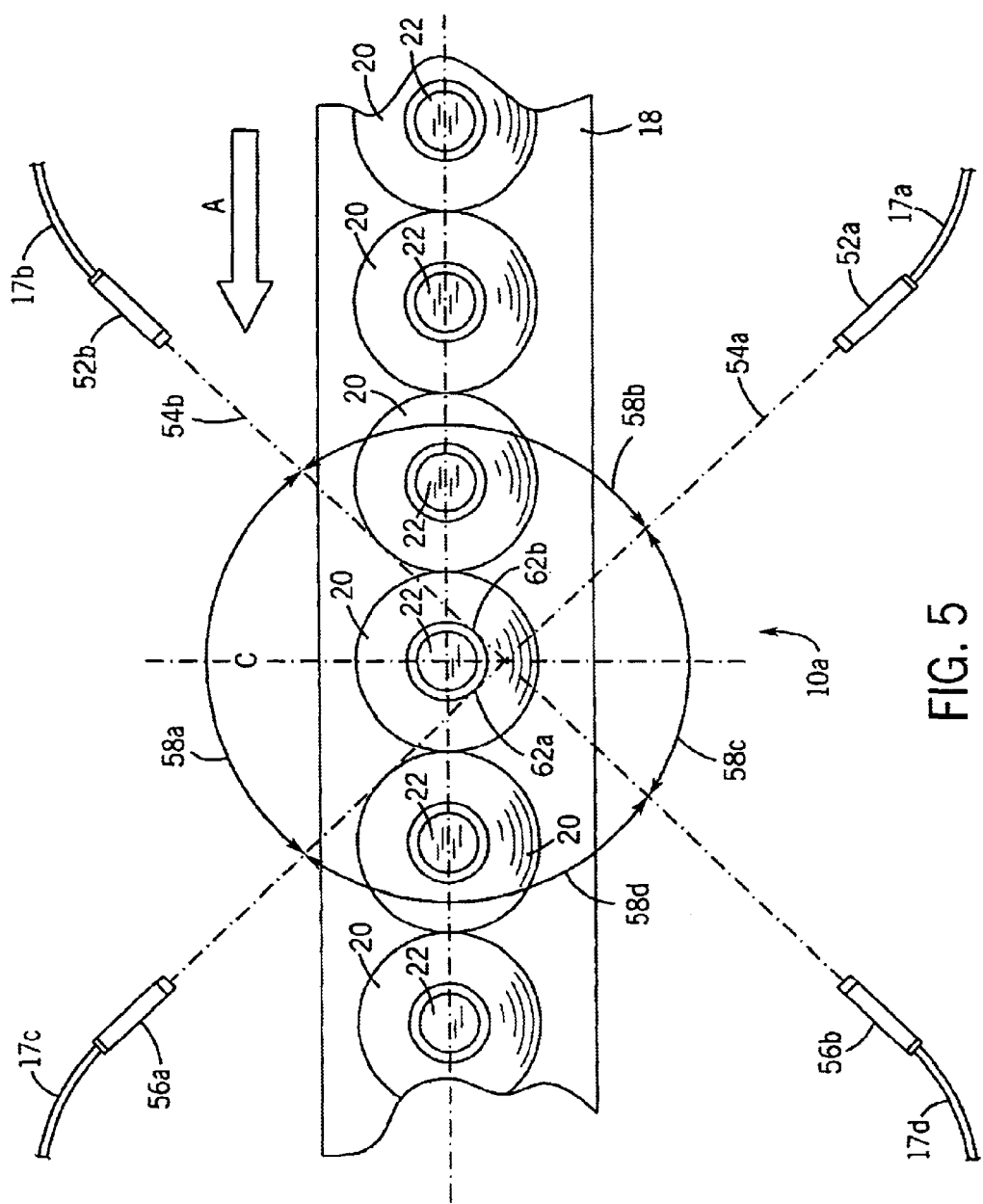
FIG. 5 is a plan view of an alternate embodiment of the present invention.

FIGS. 5 and 5a illustrate an alternate embodiment of the present invention. In miscapped bottle detection device 10a, the top edge of pilfer ring 26 of bottle 20 defines height N relative to bottle 20. Alternatively, height N can also be defined as the bottom of properly placed cap 22a relative to bottle 20 when bottle 20 does not have pilfer ring 26. Emitters 52a and 52b of detection device 50 are positioned so that signal beams 54a and 54b are at proximate height N relative to bottle 20 and normal to axis B. Furthermore, emitters 52a and 52b are positioned so that signal beams 54a and 54b traverse pilfer ring 26 at tangent points 62a and 62b, respectively. Intersect angles 58a, 58b, 58c and 58d may range from about 30 degrees to about 150 degrees. Preferably, emitters 52a and 52b are positioned so that tangent points 62a and 62b are 180 degrees apart from each other along the arc defined by the outermost circular perimeter defined by bottle cap 22.

Conveyor 18 transports bottle 20 having cap 22 to detection point C as shown in FIG. 5. A sensor (not shown) operatively connected to the controller sends a signal to the controller that bottle 20 is located at detection point C. The controller then signals emitters 52a and 52b to emit signal beams 54a and 54b, respectively. Detection of signal beams 54a and 54b by signal detectors 56a and 56b, respectively, depends upon the placement of cap 22 upon bottle 20.

FIG. 6 shows the beam detection profile for cap 22a when properly placed upon bottle 20. Emitters 52a and 52b direct signal beams 54a and 54b (shown partially in phantom) to tangent points 62a and 62b, respectively, just above pilfer ring 26. Since the bottom of cap 22a abuts pilfer ring 26, cap 22a prevents signal detectors 56a and 56b from detecting signal beams 54a and 54b, respectively. The controller is programmed to interpret this absence of detection as a properly capped bottle. Hence, the controller in this situation generates no miscapped bottle indicia. In the event the design of bottle 20 does not permit properly placed cap 22a to fully block signal beams 54a and 54b from detectors 56a and 56b, respectively, a signal beam detection threshold may be programmed into the controller. This threshold establishes a minimal signal that constitutes a valid detection. Thus, some degree of signal may be detected by detectors 56a and 56b yet still be interpreted by the controller as the absence of detection thereby identifying a properly placed cap.

FIG. 7 illustrates the beam detection profile for high cap 22b. As the bottom of high cap 22b is above height N, signal beams 54a and 54b traverse tangent points 62a and 62b, respectively, and are detected by signal detectors 56a and 56b, respectively. Correspondingly, the controller is programmed to generate a signal indicating a high capped or miscapped bottle.

FIG. 8 depicts the beam detection profile for cocked cap 22c. A portion of cocked cap 22c abuts pilfer ring 26 at tangent point 62a and blocks signal beam 54a (shown in phantom) from being detected by signal detector 56a. The bottom of cocked cap 22c, however, is above height N at tangent point 62b. This allows signal beam 54b to traverse tangent point 62b and be detected by signal detector 56b. With this detection, the controller is programmed to generate a signal indicating a cocked cap or an otherwise miscapped bottle.

Figure 9:
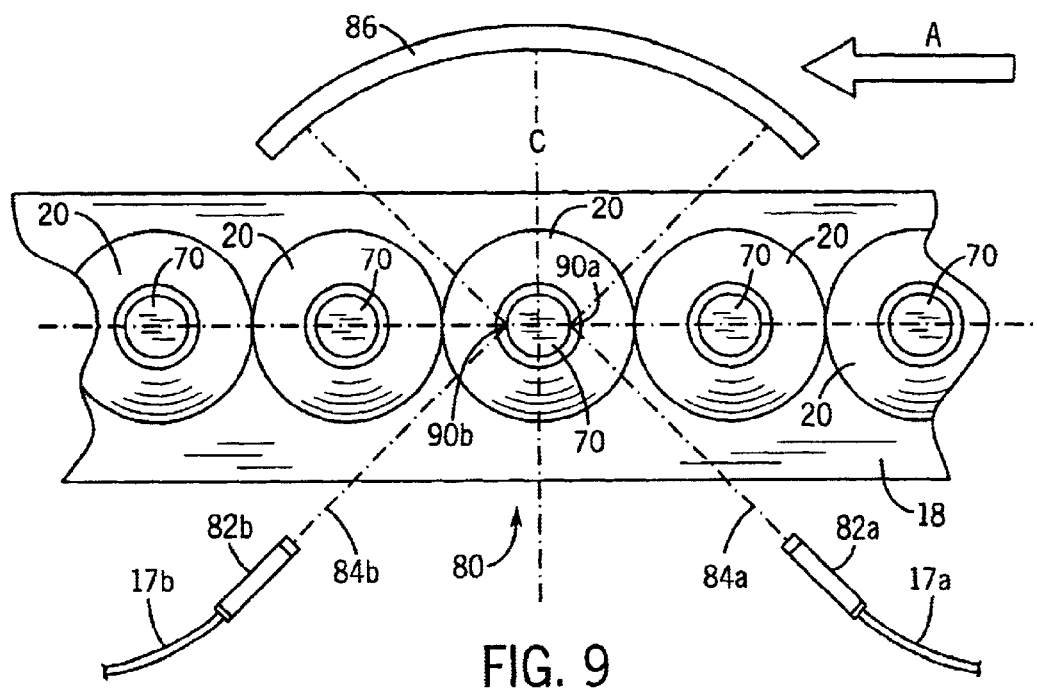
FIG. 9 is a plan view of an alternate embodiment of the present invention.
Figure 9A:
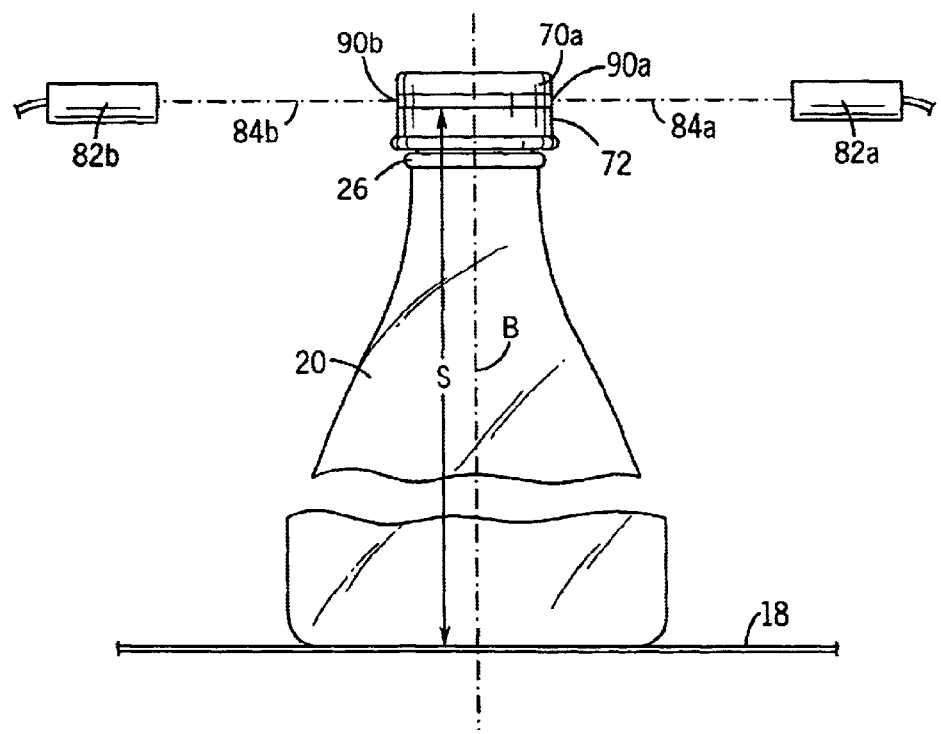
FIG. 9a is a side view of a properly capped bottle in accordance with an alternate embodiment of the present invention.

FIGS. 9 and 9a depict an alternate embodiment of the present invention, wherein bottle cap 70 comprises reflective band 72. Reflective band 72 extends circumferentially around a portion of the axial surface of cap 70. When properly placed cap 70a is upon bottle 20, reflective band 72 also defines the height of a properly placed cap S relative to bottle 20 as shown in FIG. 9a.

Reflective band 72 may be made of any suitably adapted reflective material. Reflective band 72 may be integral to and constructed of the same material as cap 70. Alternatively, reflective band 72 may comprise a reflective material that is affixed to bottle cap 70 in any manner commonly known to the skilled artisan. This material may include, but is not limited to, plastic, metal, glass or any combination thereof.

Preferably, bottle cap 70 is a resilient polymer plastic with reflective band 72 integral thereto and having a smooth reflective surface.

Miscapped bottle detection device 80 comprises emitter 82a and 82b which emit signal beams 84a and 84b, respectively. Emitters 82a and 82b are positioned so that signal beams 84a and 84b are at proximate height S relative to bottle 20 and normal to vertical bottle axis B as shown in FIG. 9a. Emitters 82a and 82b are located on the same side of conveyor 18. A single signal detector 86 is located on the opposing side of conveyor 18 and is positioned to detect the absence or presence of reflected beams 84a and 84b.

Conveyor 18 transports bottle 20 having cap 70 to detection point C as shown in FIG. 9. A sensor (not shown) operatively connected to the controller sends a signal to the controller that bottle 20 is located at detection point C. The controller then instructs emitters 82a and 82b to emit signal beams 84a and 84b, respectively. Emitters, 82a and 82b are positioned so that signal beams 84a and 84b, respectively, contact the axial surface of bottle cap 70 at different target points 90a and 90b, respectively. To detect substantially all permutations of a miscapped bottle regardless of its radial orientation, the radial arc separating target points 90a and 90b on cap 70 is preferably between about 45 degrees to about 180 degrees. FIG. 9 illustrates the most preferred arrangement wherein target points 90a and 90b are 180 degrees apart from each other along the radial arc of cap 70. Detection of signal beams 84a and 84b by signal detector 86 depends upon the placement of cap 70 upon bottle 20.

Figure 10:
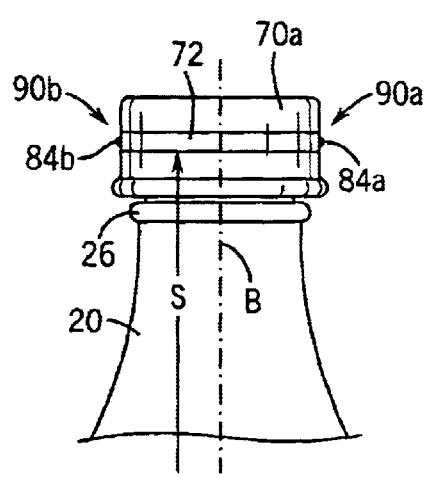
FIG. 10 is a side view of the detection of a proper cap in accordance with an alternate embodiment of the present invention.

FIG. 10 illustrates the beam detection profile for a properly placed cap 70a on bottle 20. Emitters 82a and 82b direct signal beams 84a and 84b, respectively, to contact the side of cap 70a at target points 90a and 90b, respectively. Both target points 90a and 90b contact bottle cap 70a on reflective band 72. Signal beams 84a and 84b are thereby reflected to detector 86 wherein detection occurs. Detector 86 is preferably curved to more readily detect signal beams 84a and 84b. A curved detector 86 also allows more flexibility for the placement of emitters 82a and 82b. Preferably, signal beam 84a is at a different frequency and/or wavelength than 84b to avoid interference. As such, detector 86 may be any signal detector commonly known to those skilled in the art that can detect multiple signals at different frequencies and/or wavelengths. The controller is programmed to interpret this detection profile as a properly capped bottle. A corresponding signal indicating a properly capped bottle may be generated as desired.

Figure 11:
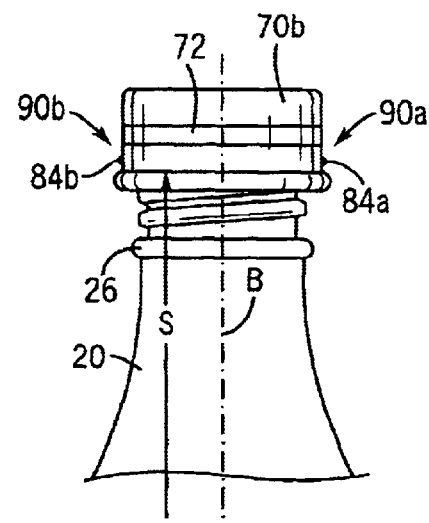
FIG. 11 is a side view of the detection of a high cap in accordance with an alternate embodiment of the present invention.

FIG. 11 shows the beam detection profile for high cap 70b on bottle 20. Reflective band 72 is above height S. Signal beams 84a and 84b contact bottle cap 70b at target points 90a and 90b, respectively, at non-reflective regions of bottle cap 70b. As such, signal beams 84a and 84b are either absorbed or dispersed by cap 70b. Signal beams 84a and 84b are not reflected by reflective band 72 and no signal detection occurs by detector 86. The controller is programmed to interpret this absence of detection as a miscapped bottle. Correspondingly, a signal may be generated to indicate a miscapped bottle.

Figure 12:
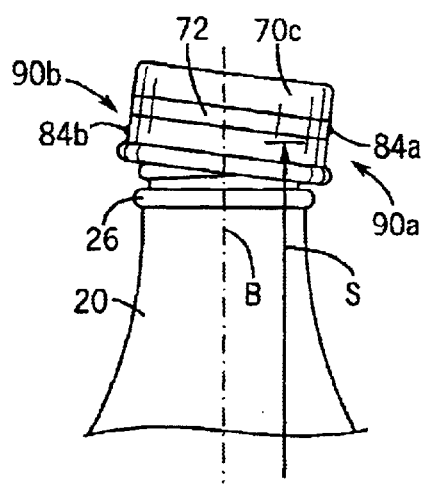
FIG. 12 is a side view of the detection of a cocked cap in accordance with an alternate embodiment of the present invention.

FIG. 12 depicts the beam detection profile for cocked cap 70c. A portion of reflective band 72 is at height S. Hence, target point 90a for signal beam 84a occurs on reflective band 72. Signal beam 84a is thereby reflected to detector 86 for detection. A portion of reflective band 72, however, is above height S. Target contact point 90b for signal beam 84b thereby contacts cocked cap 70c at a non-reflective portion. Signal beam 84b is either dispersed or absorbed by the non-reflective portion of cocked cap 70c and not detected by detector 86. The controller is programmed to interpret this detection profile as a miscapped bottle. A signal may be generated to indicate a miscapped bottle.

Figure 13:
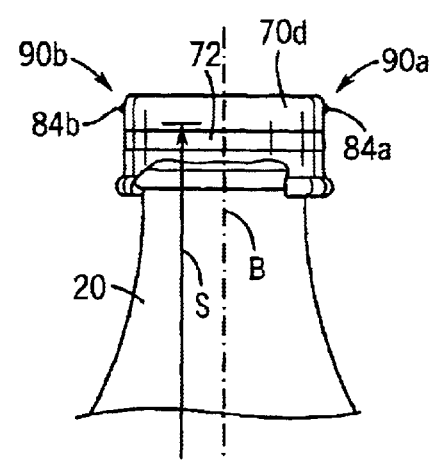
FIG. 13 is a side view of the detection of a low cap in accordance with an alternate embodiment of the present invention.

FIG. 13 depicts the beam detection profile for low cap 70d. Reflective band 72 on low cap 70d is below height S. As such, target points 90a and 90b for signal beams 84a and 84b, respectively, occur at non-reflective regions of low cap 70d. Signal beams 84a and 84b are either dispersed or absorbed by these non-reflective regions of low cap 70d. Detector 86 therefore detects neither signal beam 84a nor signal beam 84b. The controller is programmed to interpret this detection profile as a miscapped bottle. A corresponding signal to indicate a miscapped bottle may be generated as desired. Alternatively, band 72 could be non-reflective or dispersive and adjacent cap regions reflective, in which case the detection of a reflected signal would be indicative of an improperly positioned cap and the non-detection of a signal indicative of a correctly positioned cap.

Figure 14:
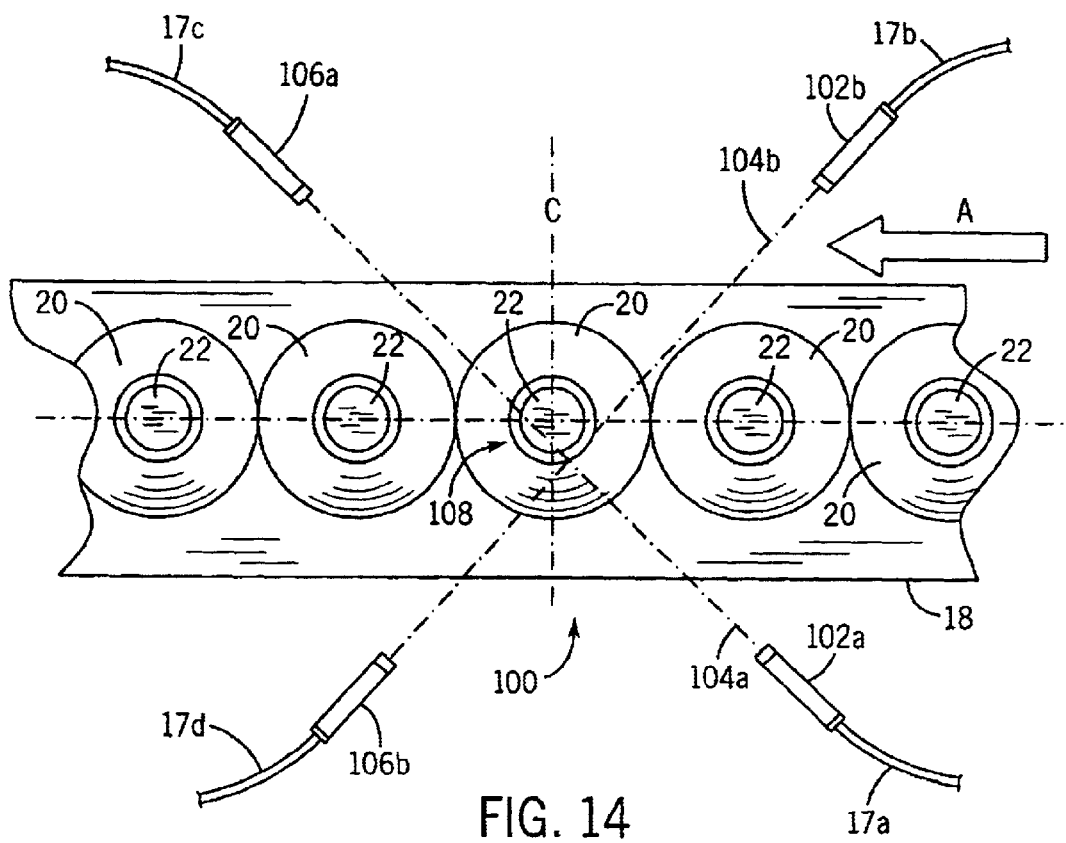
FIG. 14 is a plan view of a further alternate embodiment of the present invention.
Figure 14A:
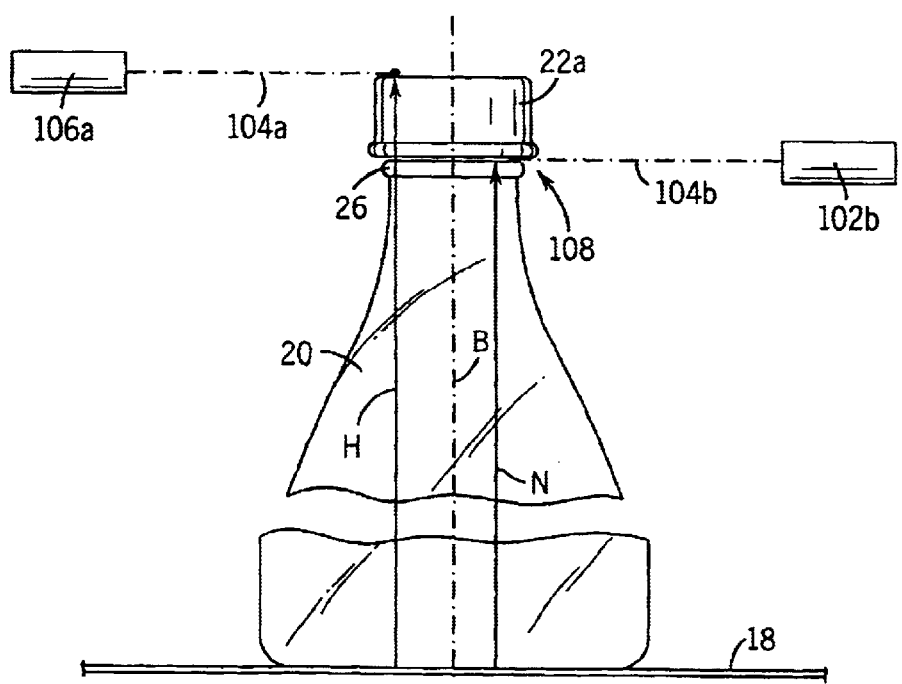
FIG. 14a is a side view of a properly capped bottle in accordance with an alternate embodiment of the present invention.

FIGS. 14 and 14a depict an alternate embodiment of miscapped bottle detection device 100 wherein emitter 102a, signal beam 104a and signal detector 106a are all positioned at relative height H. Emitter 102b, signal beam 104b and signal detector 106b are also positioned at relative height N. Emitter 102a is non-planar in relation to emitter 102b. Emitters 102a and 102b are normal to axis B and are preferably on opposing sides of conveyor 18. Emitters 102a and 102b are further positioned so that signal beams 104a and 104b would intersect if in the same plane. Preferably, the angles between skewed beams 104a and 104b is 90 degrees.

As emitter 102a is proximately located at height H, signal beam 104a traverses the plane defined by the top of properly placed cap 22a. As emitter 102b is located at proximate height N, signal beam 104b traverses the top of pilfer ring 26 at tangent point 108. Detection of signal beams 104a and 104b by signal detectors 106a and 106b, respectively, depends upon the placement of cap 22 upon bottle 20.

Figure 15:
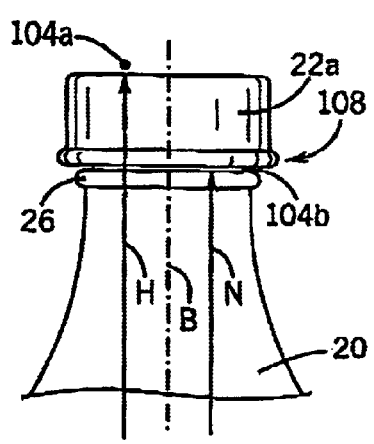
FIG. 15 is a side view of the detection of a properly capped bottle in accordance with an alternate embodiment of the present invention.

FIG. 15 shows the beam detection profile for properly placed cap 22a upon bottle 20. Signal beam 104a traverses the plane defined by the top of cap 22a at height H. Signal beam 104a is subsequently detected by detector 106a. Signal beam 104b (shown in phantom) is blocked as the bottom of cap 22a abuts pilfer ring 26 (at height N) at tangent point 108. The controller is programmed to interpret this detection profile as a properly capped bottle.

Figure 16:
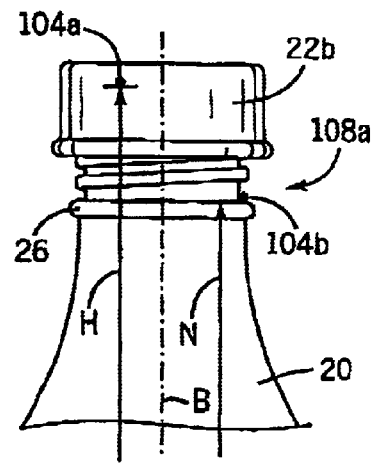
FIG. 16 is a side view of the detection of a high cap in accordance with an alternate embodiment of the present invention.

FIG. 16 illustrates the beam detection profile for high cap 22b upon bottle 20. High cap 22b extends beyond height H thereby blocking signal beam 104a from detection by detector 106a. The bottom of high cap 22b is above height N and signal beam 104b traverses tangent point 108 and is detected by detector 106b. The controller is programmed to interpret this detection profile as a miscapped bottle.

Figure 17:
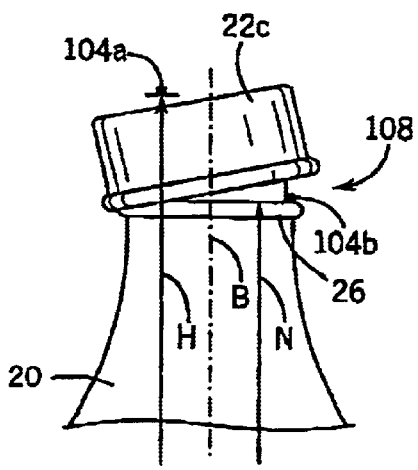
FIG. 17 is a side view of the detection of a cocked cap in accordance with an alternate embodiment of the present invention.
Figure 17A:
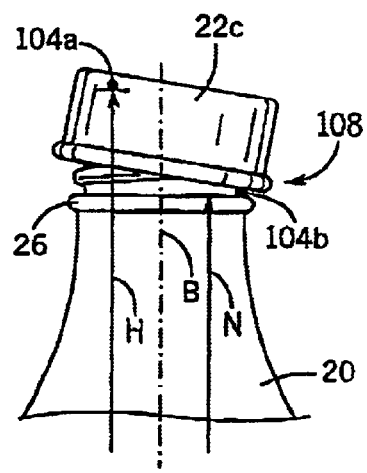
FIG. 17a is a side view of the detection of a cocked cap in accordance with an alternate embodiment of the present invention.

FIGS. 17 and 17a show two beam detection profiles for cocked cap 22c. FIG. 17 depicts cocked cap 22c riding bottle 20 so that signal beam 104a traverses the top of cap 22c and is readily detected by detector 106a. Signal beam 104b, however, traverses bottle 20 at tangent point 108 and is detected by detector 106b. The controller is programmed to interpret this detection profile as a cocked capped or miscapped bottle.

FIG. 17a depicts a second permutation for cocked cap 22c. Signal beam 104a is blocked by cocked cap 22c preventing detection from detector 106a. The bottom of cocked cap 22c abuts pilfer ring 26 at tangent point 108 thereby blocking signal beam 104b (shown partially in phantom) from detection by detector 106b. The controller is programmed to interpret this detection profile as a cocked cap or miscapped bottle.

While the invention has been described with respect to certain preferred embodiments, as will be appreciated by those skilled in the art, it is to be understood that the invention is capable of numerous changes, modifications and rearrangements and such changes, modifications and rearrangements are intended to be covered by the following claims.

What is claimed is:

1. An apparatus for detecting whether a capped bottle has an incorrectly positioned cap for use in a bottle line, regardless of the radial orientation of the cap, comprising:
    a bottle cap position detector system for sensing the bottle cap position, the detector system comprising two signal emitters, each of said signal emitters capable of directing a detectable signal;
    a signal detector capable of detecting the presence or absence of a signal from each of said signal emitters;
    each of said signal emitters positioned to direct a signal to a different cap target location with respect to a capped bottle to be tested in which a correctly positioned cap on the bottle defines a vertical cap axis and a correct cap height relative to the bottle, the signals being directed in a plane normal to vertical cap axis, each signal directed at a predetermined height relative to the cap and said signals radially spaced from each other relative to the circumference of a correctly positioned cap so that the presence or absence of a signal detected by said signal detector when the signals are emitted by the signal emitters is indicative of one or more incorrect cap positions sensed during detection with respect to a bottle selected from the group consisting of high cap, low cap and cocked cap, regardless of the radial orientation of the cap.

2. The apparatus of claim 1 wherein said emitters substantially simultaneously direct a detectable signal to said detector.

3. The apparatus of claim 1 wherein said signal comprises focused light.

4. The apparatus of claim 3 wherein said focused light is selected from the group consisting of laser, x-ray, visible, ultra-violet, infrared or far red.

5. The apparatus of claim 1 wherein detection of an emitter signal by the signal detector indicates an improperly capped bottle.

6. The apparatus of claim 1 wherein non-detection of a signal by the signal detector indicates an improperly capped bottle.

7. The apparatus of claim 1 wherein the target location is selected from the group consisting of the cap top, the cap bottom, the cap side or combinations thereof.

8. The apparatus of claim 1 wherein the angle of radial spacing between emitters is from about 45 degrees to about 135 degrees.

9. The apparatus of claim 1 wherein the angle of radial spacing between emitters is about 90 degrees.

10. The apparatus of claim 1 wherein said emitted signals are proximately directed above or below the group consisting of the cap top, a tangent point below the cap, the cap side or combinations thereof.

11. The apparatus of claim 1 wherein said bottle cap further comprises a reflective band circumferentially extending around the axial surface of said cap.

12. The apparatus of claim 11 wherein said signal is directed at target locations on the reflective band and the presence or absence of a signal reflected off of the reflective band constitutes detection.

13. A method of detecting whether a capped bottle has an incorrectly positioned cap, regardless of the radial orientation of the cap, comprising the steps of:
    providing a detector system comprising two signal emitters, each of said signal emitters capable of directing a detectable signal and a signal detector capable of detecting the presence or absence of a signal from each of said signal emitters;
    positioning each signal emitter to direct a signal to a different cap target location with respect to a capped bottle to be tested in which a correctly positioned cap on the bottle defines a vertical cap axis and a correct cap height relative to the bottle;
    directing said signals in a plane normal to the vertical cap axis, each signal directed at a predetermined height relative to the cap;
    radially spacing said signals from each other relative to the circumference of a correctly positioned cap;
    indicating whether the presence or absence of a signal detected by said signal detector when the signals are emitted by the signal emitters is one or more incorrect cap positions selected from the group consisting of high cap, low cap and cocked cap.

* * * * *